United States Patent [19]

Jiang et al.

[11] Patent Number: 5,436,357

[45] Date of Patent: Jul. 25, 1995

[54] POLYMER SUPPORTED ORGANOTIN CATALYST

[75] Inventors: Qian Jiang, Lansdale; Christine McDade, North Wales; Andrew W. Gross, Hatboro, all of Pa.

[73] Assignee: Rohm and Haas Company, Philadelphia, Pa.

[21] Appl. No.: 254,809

[22] Filed: Jun. 6, 1994

[51] Int. Cl.$^6$ .............................................. C07F 7/22
[52] U.S. Cl. .................................................. 556/95
[58] Field of Search .......................................... 556/95

[56] References Cited

U.S. PATENT DOCUMENTS 3,305,388  2/1967  Waack ................................. 556/95
3,975,334  8/1976  Weinshenker ........................ 526/19

FOREIGN PATENT DOCUMENTS 1118135  11/1965  Germany.

OTHER PUBLICATIONS

Polymer-Supported Catalysts in Nucleophilic Addition of n-butanol to Isocyanates, Journal of Molecular Catalysts, 64 (1991), 15–22, P. A. Berlin, M. A. Levina, R. P. Tiger and S. G. Entelis, Institute of Chemical Physics, Moscow 117977 (U.S.S.R.).

Polymer-Supported Lewis Acid Catalysts, VI Polystyrene-Bonded Stannic Chloride Catalyst, vol. 9, No. 1, 79–85, Chinese Journal of Polymer Science, Ran Ruicheng, FU Diankui, 1991.

Organic Chemistry, vol. 56, No. 21, Oct. 11, 1991, A Polymer Supported Organotin Hydride and Its Multipurpose Application in Radical Organic Synthesis, M. Gerlach, F. Jordens, H. Kuhn, W. P. Neumann, and M. Peterseim.

Polymer-Supported Lewis Acid Catalysts, IV. Complexes of Stannic Chloride and a Functional Polymeric Carrier, R. C. Ran and G. P. Mao, Department of Chemistry, Peking University, Beijing 100871, People's Republic of China, J. Macromol., S.C.I.—Chem. A27(2), pp. 125–136 (1990).

*Primary Examiner*—Joseph L. Schofer
*Assistant Examiner*—Wu C. Cheng
*Attorney, Agent, or Firm*—Jordan J. Driks; Richard A. Haggard

[57] ABSTRACT

A tetravalent organotin containing compound where the tin atom is attached via an alkyl group to a phenyl moiety with a polymerizable group thereon, is useful as a monomer. A polymer prepared from the monomer. A transesterification catalyst prepared from the polymer and a process for conducting a transesterification reaction using the transesterification catalyst.

7 Claims, No Drawings

POLYMER SUPPORTED ORGANOTIN CATALYST

BACKGROUND OF THE INVENTION

This invention relates to a tetravalent tin containing monomer. More particularly, this invention relates to a monomer as aforesaid, a polymer prepared from said monomer and a catalyst prepared from said polymer which is useful for transesterification and a process for conducting a transesterification reaction.

Heterogeneous catalysts are known. They are advantageous when used in a transesterification reaction because the catalyst may easily be separated from the reaction mixture whereas additional steps are necessary to separate a homogeneous catalyst from the reaction mixture.

Known polymeric organotin compounds are not effective in catalyzing transesterification reactions because of their lack of selectivity for the desired reaction and the fact that the tin tends to leach out too quickly from the polymer so that only a very few transesterification reactions may be conducted using a polymeric organotin compound.

Polymeric organotin compounds may be prepared from polymerizable tin containing monomers.

Known tetravalent tin containing monomers are not suitable for preparing the transesterification catalysts of this invention because they either do not have the desired functionality for transesterification and the monomer cannot be modified to contain such functionality or the tetravalent tin containing monomer decomposes during polymerization.

It is an object of this invention therefore, to produce a tetravalent tin containing monomer wherein at least one of the ligands is a labile group subject to a specific functionalization.

Another object of this invention is to prepare a polymer, from the monomer, which is a useful in preparing a transesterification catalyst.

A further object of this invention is to prepare a transesterification catalyst which has a high selectivity, high activity and long catalyst life which may be used in a transesterification reaction.

Yet another object of this invention is to provide a process for conducting a transesterification reaction.

Other objects and advantages will become apparent from the following more complete description and claims.

SUMMARY OF THE INVENTION

Broadly, this invention contemplates a composition of matter comprising:

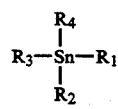

wherein $R_4$ is

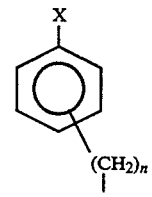

and X is a polymerizable group, n is a number from 2 to 12;

$R_1$, $R_2$ and $R_3$ are independently selected from the class consisting of phenyl, allyl, vinyl, naphthyl, alkyl phenyl, ($C_1$–$C_4$) alkyl, ($C_1$–$C_4$) alkylene, alkaryl, aralkyl and $R_4$ and at least one of $R_1$, $R_2$ and $R_3$ is phenyl, benzyl, allyl or vinyl.

This invention further contemplates a transesterification catalyst comprising: a polymer having a repeating unit (the term "repeating unit" means at least two of the units set forth below on the polymer chain) comprising:

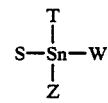

wherein T is

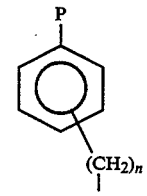

and P is the polymer backbone derived from a polymerizable group, n is a number from 2 to 12;

S, W and Z are independently selected from a halogen, (such as chloro, bromo, fluoro or iodo), phenyl, allyl, vinyl, naphthyl, alkyl phenyl, ($C_1$–$C_4$)alkyl, ($C_1$–$C_4$)alkylene, alkaryl, aralkyl and alkoxy group and T, and at least one of Z, S or W is an alkoxy group.

This invention also contemplates a process for conducting a transesterification reaction comprising the steps of reacting, at a temperature of from about 50° C. to about 150° C., in the liquid phase, an ester with an alcohol in the presence of a solid polymeric heterogeneous tin alkoxide containing catalyst and removing the liquid phase, containing the transesterification product, from the heterogeneous catalyst.

DETAILED DESCRIPTION

The composition of matter, a monomer, is used to prepare the polymer from which the transesterification catalyst is prepared and which is used in practicing the process of this invention.

The monomer may be prepared by reacting a tetravalent organotin hydride compound with a phenyl compound which has a reactive site and a polymerizable group. The reaction is carried out in the presence of a catalyst at an elevated temperature and in an inert atmosphere.

For example, one may react triphenyltin hydride with more than one equivalent of divinylbenzene in the presence of a catalyst such as 2,2-azo-bis-isobutyronitrile at an elevated temperature.

The reaction is considered complete when the tin-hydrogen absorption in the infrared spectrum at about 1850 cm$^{-1}$ disappears, for example, after a period of from about 4 to about 30 hours. The resultant monomer is vinylphenylethyl triphenyltin with divinylbenzene being present. The reaction results in the saturation of one of the vinyl groups of the divinylbenzene while leaving a vinyl group attached to the phenyl group so that the composition of matter is polymerizable.

The reaction is generally conducted in an inert atmosphere, such as nitrogen, at a temperature of from about 20° C. to about 70° C. and preferably from about 35° C. to about 50° C.

In place of a hydride, which is reacted with the divinylbenzene, to prepare the monomer of this invention, one may use a dihydride and the like.

The tetravalent tin hydride may be reacted with any compound which will allow the tetravalent tin compound to be linked to a polymerizable group such as a styrenic group. It has been found that crosslinking agents and graft linking agents are useful in preparing the composition of matter of this invention. For example, in place of divinylbenzene, one may use other polyvinyl compounds which have at least two active vinyl groups such as trimethylpropane trimethacrylate, diethylene glycol divinyl ether, ethylene glycol dimethacrylate, divinyltoluene, trivinylbenzene, divinylchlorobenzene, divinylpyridine, divinylnaphthalene and the like.

It is preferred however to use divinylbenzene as the crosslinking agent.

When preparing the monomer, the tetravalent tin hydride and the crosslinking or graft linking agent is used in a ratio of one mole of tin hydride to one to four moles of crosslinking or graft linking agent.

Generally, the graft or crosslinking agent is used in excess of the stoichiometric amount required in order to assure that the resultant composition will have a polymerizable group thereon, so that the polymer may then be prepared.

In place of the azo-bis-isobutyronitrile catalyst used to prepare the monomer of this invention, one may use any catalyst which is a non-oxidizing free radical initiator. For example, one may use compounds from the azo-nitrile family of compounds such as 2,2'-azo-bis-(2,4-dimethylpentane)nitrile; 1,1-azo-bis-cyclohexane nitrile; and other azo derivatives such as 2',2'-azo-bis-isobutane, triazobenzene; and tetrazene compounds such as 1,4-dimethyl-1,4-diphenyl-tetrazene-2; and the like.

Thus, one may use any of the foregoing catalysts to conduct the reaction between the tetravalent tin hydride and the crosslinking or graft linking agent.

The polymer is prepared from the monomer composition whose preparation has been described above.

The polymer of this invention may be prepared from the aforedescribed monomer by either suspension polymerization, emulsion polymerization, solution polymerization or bulk polymerization.

It is preferred that the polymer be prepared by suspension polymerization because beads of a preferred size for conversion to a heterogeneous transesterification catalyst are thereby obtained.

When polymerizing the monomer of this invention, a vinyl-containing comonomer, may be present. Among such comonomers which may be present are styrene, divinylbenzene, vinyltoluene, vinylnaphthalene, ethylvinyl benzene, and the like; and acrylates/methacrylates such as ethyl acrylate, methyl methacrylate, butyl acrylate, butyl methacrylate, and vinyl acetate, vinyl pyridine and the like.

The amount of vinyl containing comonomer present may vary widely up to about 95 mole percent of the monomer plus comonomer. It is preferred, however, that if a comonomer is present, it be present in an amount of from about 30 to about 60 mole percent.

When the polymer is prepared by suspension polymerization, an aqueous dispersion medium is often used. The aqueous phase generally contains a dispersant such as xanthan gum (a biosynthetic polysaccharide), poly(-diallyldimethyl ammonium chloride), polyacrylic acid and salts thereof such as the sodium salt, polyacrylamide, magnesium silicate, hydrolyzed poly(styrene-maleic anhydride) and the like; protective colloids such as carboxymethyl cellulose, hydroxyalkyl cellulose, methyl cellulose, polyvinyl alcohol, gelatin and the like; buffering agents such as phosphate and borate salts and the like; and pH control chemicals such as sodium hydroxide, sodium carbonate and the like.

The organic phase generally contains the monomer, comonomer, crosslinking agent, if present, and an initiator and a water immiscible solvent. The organic phase is slowly added to the aqueous phase. A sweep of nitrogen is initiated over the reaction mixture and gentle stirring is commenced and gradually increased while increasing the reaction temperature from about 30° C. to about 100° C. The droplet size of the monomer and comonomer to be polymerized is controlled by the rate of stirring. More rapid stirring tends to favor a smaller droplet size.

When the desired droplet size has been obtained, the temperature is increased to that needed for polymerization. The droplets turn opaque, indicating that they have polymerized. The polymerization is considered complete when no more opaque beads are formed.

The droplet size, which determines the size of the polymer beads, may vary widely from about 0.02 mm to about 3.0 mm and preferably from about 0.5 mm to about 1.0 mm.

The polymer beads will contain from about 3% to about 30% tin, based on the weight of polymer, preferably from about 3% to about 15% and more preferably from about 6% to about 12%.

The transesterification catalyst is prepared from the polymer.

The polymer is suspended in a suitable organic solvent, such as tetrahydrofuran. The organic solvent is placed under an inert atmosphere, such as nitrogen and a halogen or a halogenating agent such as bromine is slowly added to the suspension over a period of time, such as thirty minutes. The temperature of the suspension is kept below room temperature, such as 0° C. in order to assure that the resultant halogenation reaction is not too vigorous. After the addition of the halogen is complete, the reaction mixture is stirred for an additional period of time until the halogen is consumed. The resin is then separated from the organic medium and dried. The resultant product is a polymeric halogen resin having mono-di or tri halo tin groups.

The halogens and halogenating agents which may be used in preparing the halogenated resin, which is an intermediate in the preparation of the final transesterification catalyst, are fluorine, chlorine, bromine and iodine, hydrogen chloride, hydrogen bromide, tin tetrachloride, and the like.

If fluorine is to be used, then the reaction vessels which are employed must be such as to be impervious to the action of fluorine on the walls of the vessel. If iodine is to be used, then the iodine is dissolved in a suitable solvent, such as tetrahydrofuran, and is used in the reaction.

It is preferred that the halogen or halogenating agent which is to be used is either bromine or hydrogen chloride because they are reactive and easily handled.

The temperature at which the halogenation reaction is conducted is dependent on the reactivity of the halogen used. For example, if one were to use fluorine, the reaction would be conducted at a lower temperature because of the vigorousness of the reaction. However, if one were to use iodine, then because of the lowered reactivity of the iodine, the reaction may be conducted at a higher temperature.

Generally, the temperature used in conducting the halogenation reaction will vary from about 0° C. to about 50° C.

The organic medium in which the tin polymer resins are suspended may vary widely. Generally, any organic medium may be used which will be inert during the reaction. For example, one may use carbon tetrachloride, tetrahydrofuran, chloroform, alkyl or aryl ethers, and the like.

Prior to converting the halogenated resins to the transesterification catalyst, the resin is purified by washing with alcohol, such as methanol and the like or, tetrahydrofuran, dimethylformamide, dimethylsulfoxide, acetone, methyl ethyl ketone, benzene, toluene, dioxane and the like.

The resin is converted to the alkoxide containing resin by placing a solution of a suitable alkoxide salt in a solvent and adding the halogenated resins to the solution. The halogenated resins are in suspension in the alkoxide salt solution. The suspension is then heated to reflux for a period from about 2 hours to about 48 hours under an inert atmosphere such as nitrogen until no further conversion is obtained. The resultant alkoxide resins are then separated and purified by an alcohol wash to remove any halogen salts which may be present.

The alkoxides of the following salts may be used in converting the halogenated resins to the alkoxide resin; lithium, sodium, potassium, ammonium, magnesium, and other alkali or alkaline earth metal salts and the like.

The alkoxide portion of the salts may vary from a methoxide to a $C_{20}$ alkoxide. It is preferred however, that the alkoxide used be a methoxide, ethoxide or butoxide.

Transesterification using the transesterification catalyst may be accomplished in the following manner.

An ester and an alcohol may be transesterified using the catalyst and process of this invention by reacting the ester with an alcohol in an organic medium in the presence of the catalyst according to this invention.

The ester and alcohol are added to an organic medium. The temperature of the transesterification reaction is maintained at from about 50° C. to about 130° C. for about 0.5 hours to about 8 hours. The reaction is terminated after the desired reaction time has expired or when no more alcohol is produced.

The liquid phase is then decanted and is analyzed by gas chromatography. A fresh charge of ester and alcohol may then be added.

Among the esters which may be used in the transesterification reaction are acetates, methacrylates, acrylates, propionates, butyrates, isobutyrates, fatty acid esters. and the like.

The alcohols which may be used generally have from 1 to 30 carbon atoms. Among the alcohols which may be used are: butanol, pentanol, isodecyl alcohol, lauryl alcohol, cetyl alcohol, stearyl alcohol, and the like. During the reaction, the alcohol formed by the transesterification reaction is removed by distillation.

In this manner, one may convert methyl isobutyrate and butyl alcohol to butyl isobutyrate.

Other conversions which may be accomplished using the catalyst and process of this invention are methyl methacrylate to: butyl methacrylate or lauryl methacrylate or cetyl methacrylate; ethyl acetate to butyl acetate or lauryl acetate or cetyl acetate; and methyl acrylate to butyl acrylate; and the like.

The catalyst may be used repeatedly for other transesterifications runs without significant leaching of the tin from the catalyst or loss of activity.

In order to more fully illustrate the nature of this invention and the manner of practicing the same, the following examples are presented.

Example 1—Preparation Of Monomer—Vinylphenylethyl triphenyltin Divinylbenzene Mixture To a 250 ml round bottomed flask equipped with a magnetic stir bar is added 28.0 grams of triphenyltin hydride, 33.0 grams of 91% divinylbenzene, and 0.26 gram of 2,2'-azo-bis-isobutyronitrile. The mixture is placed under a nitrogen blanket and heated to a temperature of from 40° to 45° C. Samples of the reaction mixture are periodically taken and subjected to infrared analysis. The reaction is terminated when the tin-hydrogen absorption at 1850 cm$^{-1}$ in the infrared spectrum disappears. This occurs after approximately 30 hours of heating the reaction mixture. The product is then stored at 0° C. until used for the preparation of the polymer.

Example 2—Preparation of Di(vinylphenylethyl) di-phenyltin/divinylbenzene Mixture The procedure of Example 1 is repeated except that 10.43 grams of diphenyltin dihydride, 21.4 grams of 91% divinylbenzene and 0.25 gram of azo-bis-isobutyronitrile are charged to the flask. The mixture is placed under a nitrogen blanket and heated as before. Samples are periodically taken for infrared analysis. The infrared absorbance for the tin hydride (1850 cm$^{-1}$) disappears after about 5 hours. The reaction is terminated and the product is then stored at 0° C. until it is used.

Example 3—Preparation Of Tin/Polymer Resin

Preparation of the aqueous phase

400 Grams of deionized water in a 1 liter four necked round bottom flask equipped with a condenser, a mechanical stirrer, a bubbler and a thermometer is sparged with nitrogen for five minutes to remove the oxygen. Gelatin, 0.60 gram, is then added to the flask and the solution is stirred at a temperature below 45° C. until the gelatin dissolves. Heating of the solution is discontinued and the solution is allowed to cool. When the temperature of the solution is below 40° C., 14 grams of poly(diallyldimethylammonium chloride) are added and the solution is stirred for 15 minutes. Boric acid, 2.0 grams is then added and the pH of the solution is adjusted to about 10 using a 50% sodium hydroxide solution.

Preparation Of The Organic Phase

To a 500 ml Erlenmeyer flask is added 60.2 grams of the catalyst/divinylbenzene monomer of Example 1, 30 grams of styrerie, 3.0 grams of diethylene glycol divinyl ether and 48 grams of 4-methyl-2-pentanol as a solvent. The solution is stirred at room temperature for about 15 minutes and 2.0 grams of lauroyl peroxide are then added and the mixture is again stirred until all the peroxide dissolves. The solution is immediately used for the polymerization.

Polymerization

The organic phase is slowly added to the 1 liter reaction flask which contains the aqueous phase prepared above. The 2 phases remain separated. The upper layer is the organic phase. A nitrogen sweep over the solution is initiated and gentle stirring is commenced. The polymerization mixture is maintained at a temperature of about 45° C. The stirring rate is slowly increased to initiate formation of monomer droplets and to control the droplet size. When the desired droplet size is achieved, as determined by visual observation, the temperature is increased to 75° C. and is maintained at 75° C. overnight. As the polymerization progresses, the monomer droplets become noticeably opaque. The polymerization is considered complete when the opaqueness of the monomer droplets becomes stable and no longer increases. Heating is then discontinued and the resultant polymer resin/water mixture is allowed to cool to room temperature. The liquid is decanted and the resins are rinsed with 3 bed volumes of deionized water, extracted with methanol overnight in a Soxhlet apparatus and vacuum dried at 50° C. The dry resin is obtained in an amount of 88.2 grams (a 93% polymer yield). The dry polymer resin is represented by the following formula:

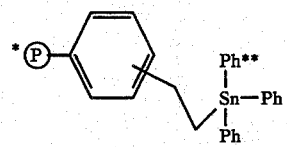

*Ⓟ = polymeric trunk
**Ph = phenyl

Elemental analysis of the resin reveals the following: (percent by weight of the resin) carbon-82.55%; hydrogen-6.99%; and tin-8.82%.

Example 4—Preparation Of Tin/Polymer Resin

Preparation of the aqueous phase

The procedure of Example 3 is repeated except that the amounts used are as follows: 150 grams of deionized water; 0.34 gram of gelatin; 7.8 grams of poly(diallyl dimethylammonium chloride); and 1.1 grams of boric acid. The pH of the solution is adjusted to about 8 using a 50% sodium hydroxide solution.

Preparation Of The Organic Phase

The procedure of Example 3 is repeated except that 30.1 grams of the monomer of Example 2 is used. The amounts of the other components used are 15 grams of styrene, 1.0 gram of diethylene glycol divinyl ether, 25 grams of 4-methyl-2-pentanol, and 0.75 gram of lauroyl peroxide.

Polymerization

The polymerization procedure of Example 3 is repeated. 42.4 grams (92% polymer yield) of dry resin is obtained. The polymer obtained may be represented by the following formula:

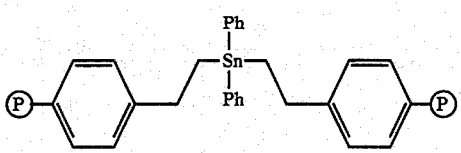

Elemental analysis of the resin reveals the following weight percentages; 83.53% carbon; 6.89% hydrogen; and 9.01% of tin.

Example 5—Preparation Of Tin Tribromide Catalyst Intermediate

To a 1 liter, 4-necked round bottom flask equipped with a mechanical stirrer, a condenser with a bubbler on top, an inlet for addition of nitrogen and an addition funnel is added 212 ml of tetrahydrofuran and 53 grams of tin polymer resin prepared as in Example 3. The suspension is stirred and cooled to a temperature of 0° C. and placed under a nitrogen blanket. Bromine, 30 grams, are added dropwise over a period of 30 minutes. After the addition, the flask is wrapped with aluminum foil and the contents of the flask are stirred for an additional six hours at room temperature. The resin is then separated and extracted in a Soxhlet apparatus with a mixture containing 80% tetrahydrofuran and 20% 1-decene. The resin is vacuum dried at 50° C. Tin bromide resin beads, 54.5 grams, are obtained and are represented by the formula:

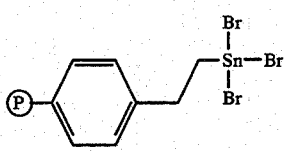

The elemental analysis of the resin (percent by weight) is as follows: 63.23% carbon; 5.43% hydrogen; 7.12% tin and 22.06% bromine.

Example 6—Preparation Of Tin Dibromide Catalyst Intermediate

The procedure of Example 5 is repeated except that the tin polymer resin used is that prepared in the manner of Example 4. The amount of components used are as follows: 40.3 grams of the tin polymer resin; 161 ml of tetrahydrofuran; and 14.1 grams of bromine. The resulting tin dibromide resin is represented by the following formula:

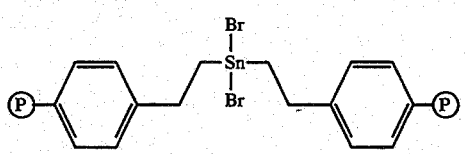

The elemental analysis of the resin (percent by weight) is as follows: 67.97% carbon; 6.45% hydrogen; 5.84% tin; and 17.75% bromine.

Example 7—Preparation Of Tin Trimethoxide Polymer Catalyst

A solution of 8.1 grams of sodium methoxide dissolved in 325 ml of anhydrous methanol and 32.4 grams of the tin tribromide resin of Example 5 are added to a 1 liter three neck round bottom flask equipped with a mechanical stirrer and a condenser. The suspension is placed under a nitrogen blanket and is heated with stirring to reflux for a period of 48 hours. The resultant resin is then separated from the liquid and is extracted overnight in a Soxhlet apparatus with methanol and then vacuum dried at 50° C. Tin trimethoxide catalyst resin, (27.9 grams) is obtained and is represented by the formula:

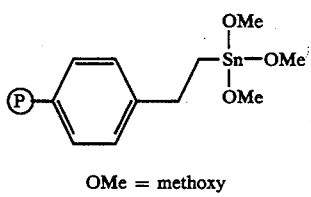

OMe = methoxy

The elemental analysis of the catalyst resin is as follows: 73.11% carbon; 6.57% hydrogen; 8.87% tin; and 5.92% bromine (bromine is present because some bromine has attached itself to the polymer backbone).

Example 8—Preparation Of Tin Dimethoxide Catalyst Resin

The procedure of Example 7 is repeated except that 7.0 gram of sodium methoxide, 400 ml of anhydrous methanol and 40 grams of the tin dibromide resin of Example 6 are used. Tin dimethoxide catalyst resin (35.9 grams) is obtained and is represented by the formula:

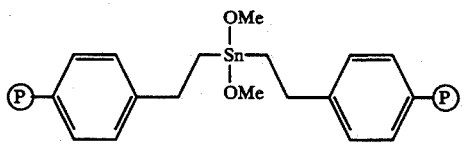

The elemental analysis (percent by weight) of the resin is as follows: 75.52% carbon; 6.98% hydrogen; 7.12% tin; and 6.83% bromine.

Example 9—Preparation Of Tin Bromodimethoxide Catalyst Resin

The procedure of Example 7 is repeated except that 5.6 grams of sodium methoxide, 740 ml of anhydrous methanol and 74 grams of the tin tribromide resin prepared as in Example 5 are used. The tin bromodimethoxide catalyst (62.8 grams) is obtained and is represented by the following formula:

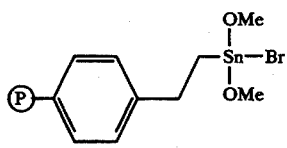

The elemental analysis (percent by weight) of the catalyst resin is as follows: 8.88% carbon; 6.43% hydrogen; 8.63% tin; and 12.11% bromine.

Example 10—Preparation Of Tin Chloro Dimethoxide Catalyst Resin

Tin trimethoxide resin, 17.2 grams prepared as described in Example 7, and 85 ml of anhydrous diethylether are placed into a 500 ml four neck round bottom flask equipped with a mechanical stirrer, a condenser and a thermometer. Stirring of the suspension is commenced and 17 ml of a 1.0 M solution of anhydrous hydrogen chloride dissolved in ether is added. The suspension is stirred at room temperature for a period of 6 hours. The resin is then separated, extracted in a Soxhlet using tetrahydrofuran and then vacuum dried at a temperature of 50° C., Tin chlorodimethoxide catalyst resin, 16.9 grams, is obtained and is represented by the formula:

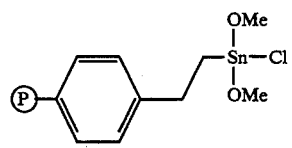

The elemental analysis of the catalyst resin is 71.94% carbon; 6.67% hydrogen; 9.89% tin; 2.77% bromine; and 3.53% chlorine.

Example 11—Transesterification Process Using A Tin Trimethoxide Catalyst Resin

Methyl isobutyrate, 131 grams, in 19 grams of n-butanol, and 10 grams of the tin trimethoxide catalyst prepared as described in Example 7 are charged to a 250 ml flask equipped with a mechanical stirrer, a distillation column with a distillation head and a thermometer. The methyl isobutyrate/n-butanol/resin suspension is heated to boiling and the methanol formed is removed by take off of a methyl alcohol/methyl isobutyrate azeotrope. The reaction is terminated after 7 hours. The liquid phase is then decanted and analyzed by gas chromatography. A fresh charge of methyl isobutyrate/n-butanol is then added to the resin for another run. A total of 24 runs were conducted with the same catalyst. For each run, the n-butanol conversion to butyl isobutyrate after seven hours is given in Table 1 below. Complete conversion may be obtained by extending the reaction time.

TABLE 1

| CONVERSION OF n-BUTANOL TO BUTYL ISOBUTYRATE | |
|---|---|
| Run Number | Percent Of Conversion |
| 1 | 92.0 |
| 2 | 57.3 |
| 3 | 50.8 |
| 4 | 44.0 |
| 5 | 37.1 |
| 6 | 43.4 |
| 7 | 41.3 |
| 8 | 42.3 |
| 9 | 40.7 |
| 10 | 36.9 |
| 11 | 35.0 |
| 12 | 35.8 |
| 13 | 40.1 |
| 14 | 43.9 |
| 15 | 39.0 |
| 16 | 29.8 |

TABLE 1-continued

CONVERSION OF n-BUTANOL TO BUTYL ISOBUTYRATE

| Run Number | Percent Of Conversion |
|---|---|
| 17 | 29.9 |
| 18 | 33.3 |
| 19 | 36.1 |
| 20 | 34.1 |
| 21 | 32.4 |
| 22 | 32.1 |
| 23 | 34.4 |
| 24 | 35.0 |

Example 12—Transesterification Reaction Using A Tin Trimethoxide Catalyst Resin

The procedure of Example 11 is repeated except that the following materials are used in place of the materials used in Example 11:131 grams of methyl methacrylate, 19 grams of n-butanol, and 10 grams of the tin trimethoxide catalyst resin prepared as described in Example 7. The reaction is terminated in 2 hours. The liquid phase is decanted and analyzed as in Example 11 and a fresh charge of methyl methacrylate/n-butanol is then added to the resins to begin another run. A total of 17 runs were conducted and the n-butanol conversion to butyl methacrylate after 2 hours is given in Table 2. Complete conversion may be obtained by extending the reaction time.

TBALE 2

CONVERSION OF n-BUTANOL TO BUTYL METHACRYLATE

| Run Number | Percent Of Conversion |
|---|---|
| 1 | 98.5 |
| 2 | 83.4 |
| 3 | 63.5 |
| 4 | 55.8 |
| 5 | 54.6 |
| 6 | 59.7 |
| 7 | 54.3 |
| 8 | 58.6 |
| 9 | 49.7 |
| 10 | 50.9 |
| 11 | 54.4 |
| 12 | 49.3 |
| 13 | 52.9 |
| 14 | 49.4 |
| 15 | 50.1 |
| 16 | 47.3 |
| 17 | 47.5 |

Example 13—Transesterification Reaction Using A Tin Dimethoxide Catalyst

The procedure of Example 12 is repeated except that the catalyst used is 10 grams of tin dimethoxide catalyst prepared as described in Example 8, The reaction is terminated in seven hours, The liquid phase is then decanted and analyzed by gas chromatography, Fresh charges of methyl methacrylate and n-butanol are then added to the catalyst resin to start another run, A total of 28 runs were conducted with the catalyst and the n-butanol conversion to butyl methacrylate after seven hours is given in Table 3.

TABLE 3

CONVERSION OF n-BUTANOL TO BUTYL METHACRYLATE

| Run Number | Percent Of Conversion |
|---|---|
| 1 | 99.9 |
| 2 | 99.8 |
| 3 | 100.0 |
| 4 | 97.8 |
| 5 | 97.3 |
| 6 | 95.4 |
| 7 | 96.5 |
| 8 | 98.0 |
| 9 | 97.5 |
| 10 | 97.1 |
| 11 | 88.5 |
| 12 | 95.7 |
| 13 | 98.5 |
| 14 | 98.8 |
| 15 | 98.5 |
| 16 | 94.7 |
| 17 | 96.7 |
| 18 | 95.5 |
| 19 | 97.6 |
| 20 | 90.5 |
| 21 | 93.0 |
| 22 | 95.3 |
| 23 | 97.3 |
| 24 | 97.2 |
| 25 | 91.6 |
| 26 | 94.4 |
| 27 | 97.4 |
| 28 | 96.6 |

Example 14—Transesterification Using A Tin Bromodimethoxide Catalyst

The procedure of Example 12 is repeated except that 10 grams of polymeric tin bromo dimethoxide resin, prepared as described in Example 9, is used. A total of 17, two hour runs were conducted and the n-butanol conversion to butyl methacrylate after hours is given in Table 4.

TABLE 4

CONVERSION OF n-BUTANOL TO BUTYL METHACRYLATE

| Run Number | Percent Of Conversion |
|---|---|
| 1 | 98.7 |
| 2 | 98.7 |
| 3 | 97.7 |
| 4 | 94.8 |
| 5 | 93.9 |
| 6 | 93.4 |
| 7 | 92.4 |
| 8 | 89.7 |
| 9 | 91.2 |
| 10 | 90.6 |
| 11 | 82.5 |
| 12 | 82.9 |
| 13 | Not Measured |
| 14 | 81.5 |
| 15 | 68.3 |
| 16 | 70.7 |
| 17 | 71.2 |

Example 15—Transesterification Reaction Using A Tin Chlorodimethoxide Polymer Catalyst Methyl methacrylate, 73 grams, 27 grams of lauryl alcohol, and 15 grams of polymeric tin chlorodimethoxide catalyst, prepared as described in Example 10, are charged to a 250 ml flask equipped with a mechanical stirrer, a distillation column with a distillation head, and a thermometer. The methyl methacrylate/lauryl alcohol/catalyst suspension is heated to boiling and the methanol formed is removed as a methyl alcohol/methyl methacrylate azeotrope. The reaction is terminated in 5 hours. The liquid phase is then decanted and analyzed by gas chromatography. A fresh charge of methyl methacrylate and lauryl alcohol is added to the resins to start another run. A total of 9 runs were conducted with the same catalyst and the lauryl alcohol conversion to lauryl methacrylate after 5 hours is given in Table 5.

TABLE 5

CONVERSION OF LAURYL ALCOHOL TO LAURYL METHACRYLATE

| Run Number | Percent Of Conversion |
| --- | --- |
| 1 | 100.0 |
| 2 | 100.0 |
| 3 | 100.0 |
| 4 | 100.0 |
| 5 | 100.0 |
| 6 | 97.7 |
| 7 | 94.1 |
| 8 | 97.2 |
| 9 | 98.7 |

While this invention has been described in terms of certain preferred embodiments, and illustrated by means of specific examples, the invention is not to be construed as limited except as set forth in the following claims:

We claim:

1. A composition of matter comprising:

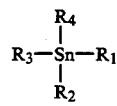

wherein $R_4$ is

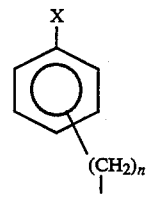

and X is a polymerizable group, n is a number from 2 to 12;

$R_1$, $R_2$ and $R_3$ are independently selected from the class consisting of phenyl, allyl, vinyl, naphthyl, alkyl phenyl, ($C_1$-$C_4$) alkyl, ($C_1$-$C_4$) alkylene, alkaryl, aralkyl and $R_4$ and at least one of $R_1$, $R_2$ and $R_3$ is phenyl, benzyl, allyl or vinyl.

2. A composition according to claim 1, wherein at least one of $R_1$, $R_2$ and $R_3$ is selected from a benzyl, phenyl, allyl or, vinyl group.

3. A composition according to claim 1, wherein n is two.

4. A composition according to claim 1, wherein X is a vinyl group.

5. A composition according to claim 1, wherein said composition is di(vinylphenylethyl) diphenyl tin.

6. A composition according to claim 1, wherein said composition is vinylphenylethyl triphenyl tin 7. A composition according to claim 1, wherein said composition is vinylphenylethyl butyl diphenyl tin.

* * * * *